United States Patent
Nakao et al.

(10) Patent No.: US 8,670,116 B2
(45) Date of Patent: Mar. 11, 2014

(54) METHOD AND DEVICE FOR INSPECTING FOR DEFECTS

(75) Inventors: Toshiyuki Nakao, Yokohama (JP); Junguo Xu, Kasumigaura (JP); Yuki Shimizu, Sendai (JP); Toshihiko Nakata, Hiratsuka (JP); Toshifumi Honda, Yokohama (JP); Yukihiro Shibata, Fujisawa (JP); Yuta Urano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/700,520

(22) PCT Filed: May 20, 2011

(86) PCT No.: PCT/JP2011/002809
§ 371 (c)(1),
(2), (4) Date: Mar. 8, 2013

(87) PCT Pub. No.: WO2012/014357
PCT Pub. Date: Feb. 2, 2012

(65) Prior Publication Data
US 2013/0155400 A1    Jun. 20, 2013

(30) Foreign Application Priority Data

Jul. 30, 2010 (JP) .................................. 2010-171331

(51) Int. Cl.
*G01N 21/95* (2006.01)
(52) U.S. Cl.
USPC .................. 356/237.2; 356/237.1; 356/237.3; 356/237.4; 356/237.5

(58) Field of Classification Search
USPC ............ 356/237.1–237.5, 394; 382/141, 144, 382/145, 149; 438/16, 18, 92, 129
See application file for complete search history.

(56) References Cited

U.S. PATENT DOCUMENTS

| | | | |
|---|---|---|---|
| 5,252,836 A * | 10/1993 | Matthews et al. | 250/559.18 |
| 5,764,793 A * | 6/1998 | Omae et al. | 382/149 |
| 5,903,342 A | 5/1999 | Yatsugake et al. | |
| 7,079,966 B2 * | 7/2006 | Knoch et al. | 702/81 |

(Continued)

FOREIGN PATENT DOCUMENTS

| | | |
|---|---|---|
| JP | 62-265147 | 11/1988 |
| JP | 9-304289 | 11/1997 |
| JP | 9-304403 | 11/1997 |
| JP | 2000-162141 | 6/2000 |

(Continued)

*Primary Examiner* — Sang Nguyen
(74) *Attorney, Agent, or Firm* — Antonelli, Terry, Stout & Kraus, LLP.

(57) ABSTRACT

A defect inspecting method is provided which comprises a pre-scan defect inspecting process including a pre-scan irradiating step for casting irradiation light onto the surface of a sample, a pre-scan detecting step for detecting the scattered lights, and a pre-scan defect information collecting step for obtaining information on preselected defects present on the sample surface on the basis of the scattered lights; a near-field defect inspecting process including a near-field irradiating step in which the distance between the sample surface and a near-field head is adjusted so that the sample surface is irradiated, a near-field detecting step for detecting near-field light response, and a near-field defect information collecting step for obtaining information on the preselected defects on the basis of the near-field light response; and a merging process for inspecting defects present on the sample surface by merging the pieces of information on the preselected defects.

16 Claims, 10 Drawing Sheets

(56) References Cited

U.S. PATENT DOCUMENTS

| | | | |
|---|---|---|---|
| 7,259,869 B2 * | 8/2007 | Hwang et al. | 356/511 |
| 8,314,929 B2 * | 11/2012 | Urano et al. | 356/237.2 |
| 8,355,044 B2 * | 1/2013 | Tsuchiya et al. | 348/92 |
| 8,514,388 B2 * | 8/2013 | Maruyama et al. | 356/237.2 |
| 2008/0151235 A1 * | 6/2008 | Oshima et al. | 356/237.4 |
| 2008/0304055 A1 * | 12/2008 | Oshima et al. | 356/237.5 |
| 2013/0097739 A1 * | 4/2013 | Zhang et al. | 850/6 |

FOREIGN PATENT DOCUMENTS

| | | |
|---|---|---|
| JP | 2000-304755 | 11/2000 |
| JP | 2006-215004 | 8/2006 |
| JP | 2007-315963 | 12/2007 |
| JP | 2008-82999 | 4/2008 |
| JP | 2008-268199 | 11/2008 |
| JP | 2009-204387 | 9/2009 |
| JP | 2010-197347 | 9/2010 |

* cited by examiner

DEFECT MAP  Haze MAP

METHOD AND DEVICE FOR INSPECTING FOR DEFECTS

TECHNICAL FIELD

This invention relates to a method and a device for inspecting fine defects existing on or in the surface of a sample at high speeds and with high precision.

BACKGROUND ART

In order to maintain and further improve the yield of products from a production line for semiconductor substrates or thin-film substrates, it is necessary to inspect defects present on or in the surfaces of a semiconductor substrate or a thin-film substrate. For example, in order to detect a fine defect of a sample, the sample surface is irradiated by a laser beam which is condensed to give on the sample surface a spot having a diameter of several tens of micrometers; the lights scattered by the fine defect is condensed and detected; and thus the fine defect having a size of, for example, several tens of nm to several μm can be detected.

As conventional techniques are known JP-A-09-304289 (Patent Literature 1) which discloses "an inspection device comprising a low elevation angle light receiving system having its optical axis at an elevation angle of not less than 30° with respect to the wafer surface and a high elevation angle light receiving system having its optical axis at an elevation angle greater than the elevation angle of the low elevation angle light receiving system, wherein the wafer is scanned by a laser beam; foreign matters are detected, as a result of scanning, by receiving the scattered laser lights with the low and high elevation angle light receiving systems; and at a single point on the wafer surface during scanning, what is detected by the high elevation angle light receiving system alone is interpreted as reflecting the defect of wafer surface while what is detected by the low elevation angle light receiving system alone or by both the low and high elevation angle light receiving systems is interpreted as reflecting a foreign matter sticking onto the wafer surface" and JP-A-2000-162141 (Patent Literature 2) which discloses "an inspection device comprising a vertical light irradiating system for casting a light beam onto the wafer surface to be inspected in the direction perpendicular to the wafer surface; an inclined light irradiating system for casting a light beam onto the wafer surface in an inclined direction; a high elevation angle light receiving system for receiving high elevation angle components of scattered lights reflected randomly from the wafer surface to be inspected; an intermediate elevation angle light receiving system for receiving intermediate elevation angle components of scattered lights reflected randomly from the wafer surface to be inspected; and a low elevation angle light receiving system for receiving low elevation angle components of scattered lights reflected randomly from the wafer surface to be inspected".

Recently, as the miniaturization of conductor patterns in LSI circuit boards has been rapidly progressing, the size of a defect to be detected has been approaching a limit of optical inspection. According to the Semiconductor Road Map, the mass production of LSI's with 25 nm nodes will be started by 2015. Accordingly, it is required for a device for inspecting wafers having no patterns to be able to detect a defect as small as a DRAM half pitch. It should be noted that defects mentioned here include fine particles sticking to the wafer surface, COP's (crystal originated particles), and scratches caused by grinding.

Known is the expression such that $I \propto d^6$, where "I" indicates the intensity of the scattered lights generated when a defect is irradiated by a laser beam, and "d" denotes the diameter of the defect. It is concluded from this expression that a decrease in the particle size steeply decreases the intensity of the scattered lights. Therefore, it is necessary to somehow augment the scattered lights emanating from the fine defect.

On the other hand, as a surface inspecting method without resorting to the detection principle using scattered lights is known Patent Literature 3 (JP-A-63-265147) which discloses "an inspecting device comprising a bump disk having bumps of a first, a second and a third heights at selected positions and having a structure identical with that of a disk to be measured; a control value generating circuit for generating control values determinative of the rotational amount of the disk to be measured; and a rotational drive mechanism for rotating the disk to be measured or the bump disk, wherein a head is first used as a reference head; after rotating the bump disk, the reference head is located at the position where the reference head comes in contact with the bump of the first height so that the first perimeter speed to give the limit of contact can be obtained; the reference head is located at the position where the reference head comes in contact with the bump of the second height so that the second perimeter speed for the bump disk to give the limit of contact can be obtained; the characteristic of the vertical distance from the disk surface of the reference head is obtained and then retained on the basis of the first and second bump heights and the first and second perimeter speeds; now the role of the reference head is changed to serve as a measuring head; the perimeter speed of the measuring head to give the limit of contact is obtained by locating at, at least, one of the bumps of the first and second heights of the bump disk; and the disk to be measured is inspected by correcting the control values such that it may give the vertical distance for the reference head, on the basis of the characteristic of the vertical distance from the disk surface of the reference head and the perimeter speed of the measuring head".

Patent Literature 3 discloses a method for inspecting the surface of a wafer, wherein a wafer to be inspected is rotated at several thousands of rpm; a detecting head having a contact sensor at its tip is located at a vertical distance of several tens of nm from the wafer surface; the entire wafer surface is scanned with the detecting head by spirally moving the wafer; and in the area where there are defects, the head comes in contact with the defects whereby the surface inspection of the wafer can be performed. With this method, in which the vertical distance of the head from the wafer surface is controlled, it becomes possible to detect a defect having a size of 10~20 nm.

CITATION LIST

Patent Literatures

Patent Literature 1: JP-A-09-304289
Patent Literature 2: JP-A-2000-162141
Patent Literature 3: JP-A-63-265147

SUMMARY OF INVENTION

Technical Problem

To follow up the miniaturization of semiconductor elements, it is required to successively improve the sensitivity in detection of inspecting devices for such semiconductor elements. According to the techniques disclosed in the Patent Literatures 1 and 2, the inspection sensitivity can be enhanced by increasing the power for the laser source. However, the increase in the laser power gives rise to the possibility that the temperature at the irradiated area on the wafer surface rises so that the irradiated area may be damaged. Also, the inspection sensitivity can be augmented by lengthening the time of laser irradiation, but this leads to the decrease in an area to be inspected per unit time and therefore to a lowered throughput. Thus, these techniques find it very difficult to inspect defects having dimensions of about 10 nm at high speeds.

Further, the inspecting device disclosed in the Patent Literature 3 is of contact type and may make scratches in the wafer surface since the detection head may drag a foreign material as a defect during inspection. Moreover, since there are usually raised defects having dimensions of several tens of nm through several μm on the wafer surface, the detecting head, whose vertical distance from the wafer surface is normally set to be several tens of nm, may hit one of the raised defects and be damaged.

Furthermore, since the disclosed inspection presupposes the contact of the inspecting head with defects, it naturally becomes very difficult to detect depressed defects such as scratches and COP's.

Solution to Problem

The gist of the representative ones of the present inventions disclosed in the present application will be explained bellow.

(1) A defect inspecting method including:
a pre-scan defect inspecting process having:
a pre-scan irradiating step for casting irradiation light onto the surface of a sample,
a pre-scan detecting step for detecting the scattered lights emanating from the area of the sample surface irradiated in the pre-scan irradiating step, and a pre-scan defect information collecting step for obtaining information on preselected defects present on the sample surface on the basis of the scattered lights detected in the pre-scan detecting step;
a near-field defect inspecting process having:
a near-field irradiating step in which the distance between the sample surface and a near-field head is adjusted on the basis of the information on the preselected defects obtained in the pre-scan defect information collecting step so that the irradiation of the sample surface is started from the position where the near-field head has been adjusted,
a near-field detecting step for detecting near-field light response generated from that area on the sample surface which is irradiated in the near-field irradiating step, and
a near-field defect information collecting step for obtaining information on the preselected defects present on the sample surface on the basis of the near-field light response detected in the near-field detecting step; and
a merging process for inspecting defects present on the sample surface on the basis of the result obtained by merging the information on the preselected defects on the sample surface obtained in the pre-scan defect information collecting step and the information on the preselected defects present on the sample surface obtained in the near-field defect information collecting step.

(2) A defect inspecting device including:
a pre-scan defect inspecting section having:
a pre-scan irradiating system for casting irradiation light onto the surface of a sample,
a pre-scan detecting system for detecting the scattered lights emanating from the area of the sample surface irradiated by the pre-scan irradiating system, and
a pre-scan defect information collecting section for obtaining information on preselected defects present on the sample surface on the basis of the scattered lights detected by the pre-scan detecting system;
a near-field defect inspecting section having:
a near-field irradiating section in which the distance between the sample surface and a near-field head is adjusted on the basis of the information on the preselected defects obtained by the pre-scan defect information collecting section so that the irradiation of the sample surface is started from the position where the near-field head has been adjusted,
a near-field detecting section for detecting near-field light response generated from that area on the sample surface which is irradiated by the near-field irradiating section, and
a near-field defect information collecting section for obtaining information on the preselected defects present on the sample surface on the basis of the near-field light response detected by the near-field detecting section; and
a merging section for inspecting defects present on the sample surface on the basis of the result obtained by merging the information on the preselected defects on the sample surface obtained by the pre-scan defect information collecting section and the information on the preselected defects on the sample surface obtained by the near-field defect information collecting section.

Advantageous Effects of Invention

This invention can provide a method and a device for inspecting defects, which can detect defects having an average size of 10~20 nanometers and inspect such defects with high sensitivity and at a high speed without damaging wafers to be inspected.

DESCRIPTION OF EMBODIMENTS

Figure 1:
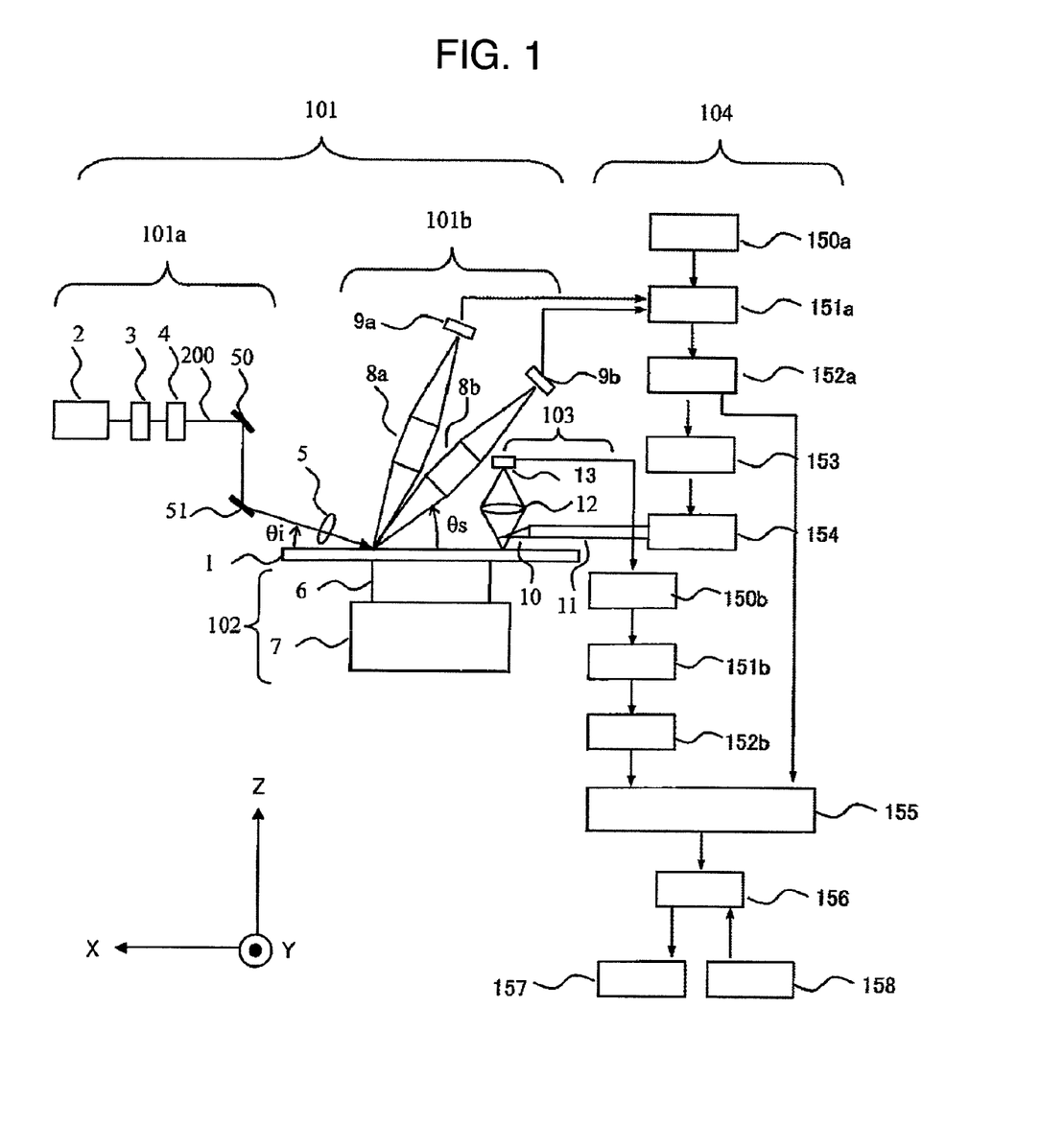
FIG. 1 schematically shows (in lateral view) the structure of a defect inspecting device according to this invention.

An embodiment of a defect inspecting device according to this invention will be described in reference to FIG. 1 (in lateral view). FIG. 1 schematically shows the structure of a defect inspecting device comprising a wafer stage 102 for supporting a wafer 1 to be inspected, thereon; a pre-scan optical system 101 for pre-scanning the wafer 1; a head slider inspecting section 103 for inspecting the wafer 1 with a head slider; and a signal processing section 104 for processing the signal obtained from the pre-scan result and by the head slider inspection.

[Pre-scan Optical System 101]

The pre-scan optical system 101 comprises an irradiation optical system 101a and a detection optical system 101b.

The irradiation optical system 101a consists mainly of a laser source 2, a beam expander 3, a polarizing element 4, mirrors 50 and 51, and a condensing lens 5. The laser beam 200 emitted from the laser source 2 has its beam diameter adjusted to a desired dimension by means of the beam expander 3, is converted to light of desired polarization by the polarizing element 4, and is cast onto the testing area of the wafer 1 at an elevation angle of θi after having been reflected by the reflecting mirrors 50 and 51 and having passed through the condensing lens 5.

It should be noted here that the laser source 2 emits a laser beam whose wavelength is 355 nm and that the elevation angle $\theta_i$ of irradiation is about 10 degrees with respect to the wafer surface. The beam spot on the testing area of the wafer 1 has a roughly elliptical shape, about 100 micrometers in the direction of the major axis and about 20 micrometers in the direction of the minor axis.

The beam expander 3 constitutes an anamorphic optical system, consisting of multiple prisms. The beam expander 3 causes the beam diameter to change only in one direction in the plane perpendicular to the optical axis so that the beam after passing the condensing lens 5 forms a roughly elliptical spot or a line-shaped brilliance on the wafer 1. Speaking of the elevation angle of irradiation, there may be a vertical irradiation system (not shown) which casts light beam onto the wafer in the nearly perpendicular direction with respect to the wafer surface.

A detection optical system 101b may consist of a plurality of detection systems, but it comprises two detection systems 8a and 8b, in an example shown in FIG. 1. The detection systems 8a and 8b are arranged with their optical axes at elevation angles $\theta_s$ different from $\theta_i$ and serve to detect the scattered lights emanating from the irradiated area of the wafer 1. The elevation angle for the detection system 8a is about 60 degrees, and the elevation angle for the detection system 8b is about 30 degrees. The associated aperture number is about 0.3.

The detection systems 8a and 8b are of the same structure, each including a condensing lens and a polarizing element (not shown), and they serve to focus the scattered lights on sensors 9a and 9b.

The polarizing element may be a polarizing filter or a polarized beam splitter (PBS), and, as a result of detecting polarized light, can reduce scattered lights (referred to as roughness-scattered lights) emanating from fine roughness in the wafer surface so that even finer defects can be detected. Further, the polarizing element is arranged to rotate about the optical axis of the detection system and detachably mounted. For example, NSPFU-30C and PBSW-10-350, both manufactured by Sigma-Koki Co. Ltd., can preferably be selected as a polarizing element and a PBS to be used here, respectively.

The sensors 9a and 9b may be implemented with photodiodes or photo-electron multiplier tubes.

[Wafer Stage 102]

The wafer stage 102 comprises a chuck for holding a wafer 1, a Z stage (not shown) for controlling the vertical position of the wafer 1, a rotating stage 6 for rotating the wafer 1, and a parallel moving stage 7 for moving the wafer 1 in a parallel shift in the direction along the X-axis. The wafer stage 102 can aid in scanning the surface of the wafer 1 in such a manner that the irradiated area on the wafer surface moves spirally on the entire wafer surface, through the combined use of rotating and parallel moving scans.

[Head Slider Inspecting Section 103]

Figure 2:
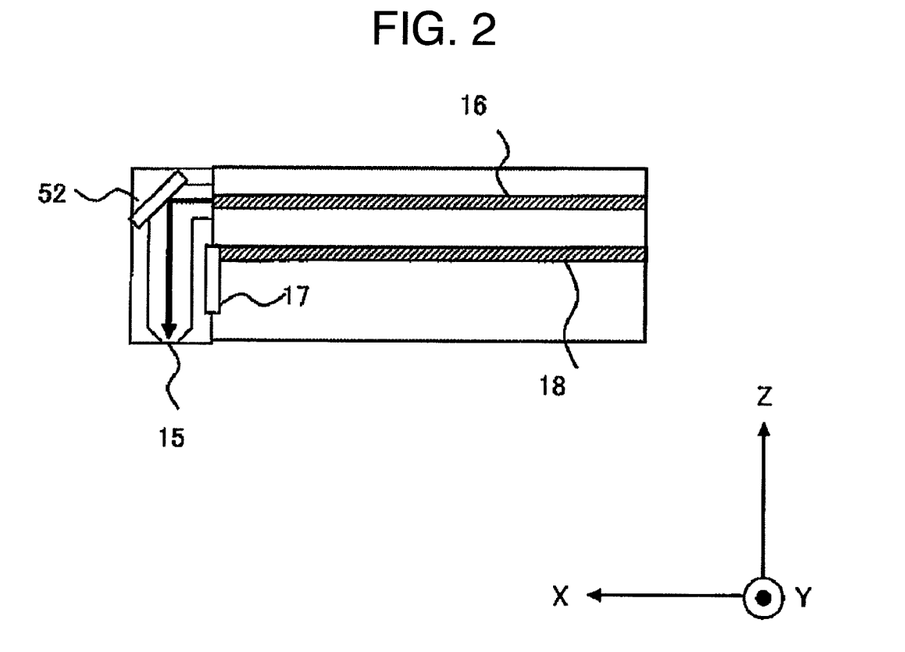
FIG. 2 schematically shows the structure of the near-field head of a defect inspecting device as a first embodiment of this invention.

The head slider inspecting section 103 comprises a near-field head 10, a head supporting mechanism 11, a near-field response detecting system 12, and a sensor 13. FIG. 2 schematically shows the structure of the near-field head of a defect inspecting device as a first embodiment of this invention.

A fine aperture 15 is cut in the front tip of the near-field head 10, and light from an external light source (not shown) is guided through a waveguide path 16, is reflected by a mirror 52, and reaches the aperture 15. The light from the external light source has a wavelength of 532 nm. The fine aperture 15 has a diameter of about 30~50 nm, which is smaller than the wavelength of irradiating light. When the guided light reaches the fine aperture 15, there is generated near-field light in the vicinity of the fine aperture 15, the beam diameter of which is of the same order as the diameter of the fine aperture 15. As described later, in this embodiment, the vertical distance of the near-field head 10 from the wafer surface is set to be about 40 nm, and near-field light having a beam diameter of about 40 nm must be produced to irradiate defects present in the wafer surface with the near-field light. Since the beam diameter of the near-field light coming out of the fine aperture is roughly equal to the diameter of the fine aperture, the diameter of the fine aperture must be set to be about 30~50 nm in this embodiment.

Although the wavelength of the external light is 532 nm and the diameter of the fine aperture 15 is about 30~50 nm in this embodiment, this is not a limitation to this invention.

The near-field head 10 incorporates therein a thermal actuator 17, which is heated by the current fed through a conductive line 18 to change the shape thereof. The thermal actuator 17 may be an actuator of bimetal type or thermal-expansion type. Since the change in shape of the thermal actuator 17 can change the distance between the near-field head 10 and the wafer surface, the vertical distance of the head from the wafer surface can be controlled.

The scattered lights generated as a result of an interaction between the near-field created by the near-field head 10 and the wafer surface, are converged by the near-field response detecting system 12, and the converged beam of the scattered lights falls on the sensor 13.

The sensor 13 may be implemented with a photodiode or a photo-electron multiplier tube. Although it is described above that the vertical distance of the head from the wafer surface can be controlled by controlling the amount of current flowing through the thermal actuator 17, the vertical distance may be controlled by using a piezoelectric element or an optical actuator.

Since the wafer stage 102 makes a rotational movement and a parallel movement simultaneously, the inspected areas for the pre-scan optical system 101 and the head slider inspecting section 103 change their positions spirally on the wafer surface. It should be noted here that the inspected areas for the pre-scan optical system 101 and the head slider inspecting section 103 are located on a straight line running through the center of the wafer 1 and nearly along the direction of the X-axis. This geometry can enable an effective inspection of the entire wafer surface.

[Signal Processing Section 104]

The signal processing section 104 comprises analog circuits 150a and 150b for performing filtering processes on the signals generated through the photoelectric conversion by the sensors 9a, 9b and 13; A/D conversion sections 151a and 151b for converting analog signals to digital signals; defect determining sections 152a and 152b for making defect determination on the basis of the obtained digital signals; a memory 153 for temporarily storing the coordinates and the sizes of defects; a vertical distance controlling section 154 for controlling the vertical distance of the near-field head from the wafer surface; an inspection result merging section 155 for merging the inspection results obtained from the pre-scan optical system 101 and the head slider inspecting section 103; a CPU 156; a map outputting section 157 for outputting a defect map and a Haze map; and an input section 158 including an interface.

Figure 3:
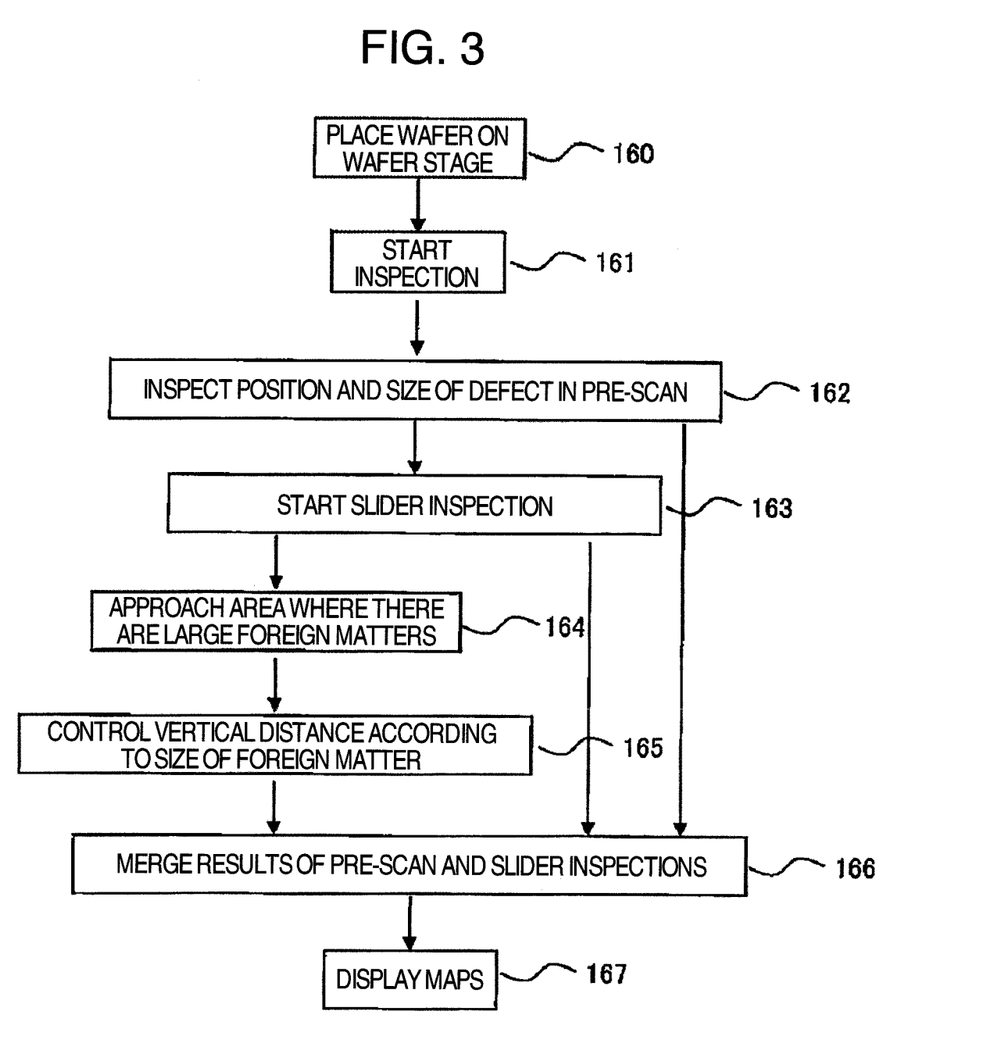
FIG. 3 is a flow chart illustrating the step flow of a defect inspecting method according to this invention.

FIG. 3 is a flow chart illustrating the step flow of a defect inspecting method according to this invention.

First, the wafer 1 is placed on the wafer stage 103 (step 160). Then, inspection recipes such as conditions for stage operations, irradiation and signal processing, are determined to start an inspection (step 161). The pre-scan optical system 101 performs pre-scan inspection, and both the sizes and the coordinates of raised defects, which are larger than a predefined specimen, are stored in the memory 153. It should be noted here that the predefined specimen is meant to be of the same dimensions as comparable to the vertical distance of the head from the sample surface. For example, it is made to be about 40 nm in this embodiment (step 162). Now, the near-field head 10 is moved above the wafer 1 to perform an inspection with the near-field head 10 (step 163). At this time, the vertical distance from the wafer surface of the near-field head 10 is about 40 nm, and if there is a raised defect having dimensions larger than about 40 nm, the near-field head 10 will collide with the raised defect. Accordingly, on the basis of the result of the pre-scan, when the near-field head 10 approaches an area including a raised defect having dimensions larger than about 40 nm (step 164), the vertical distance is adjusted in accordance with the dimensions of the raised defect such that the collision of the near-field head 10 with the raised defect can be avoided (step 165). Since defects each having dimensions larger than about 40 nm are inspected by the pre-scan optical system and since finer defects, which the pre-scan optical system cannot detect, are inspected by the near-field head 10, then the results of the two inspections are merged (step 166) so that a Defect Map and a Haze Map are both displayed (step 167).

The detailed description of steps 160~167 will be given below.

[Steps 160, 161]

After the wafer 1 has been placed on the wafer stage 102, the inspection recipes are determined. According to the inspection recipes, the rotational speed and the parallel movement speed of the wafer stage 102, the power supplied to the laser emitter in the pre-scan optical system, the elevation angle of laser irradiation, the sensitivities of sensors in the detection systems, and the vertical distance from the wafer surface of the near-field head 10 are determined.

[Step 162]

An inspection takes place with the pre-scan optical system 101.

The irradiation optical system 101a casts laser beam onto the wafer surface, the resulting irradiated spot shifts spirally over the entire surface of the wafer 1, and the scattered lights emanating from the irradiated spots are detected by the detection systems 8a and 8b. Accordingly, the sensors 9a and 9b, which receive the scattered lights, generate electrical signals whose intensities correspond to those of the scattered lights. The electrical signals are then led to the analog circuit 150a, the process by which will be described later.

Figure 4:
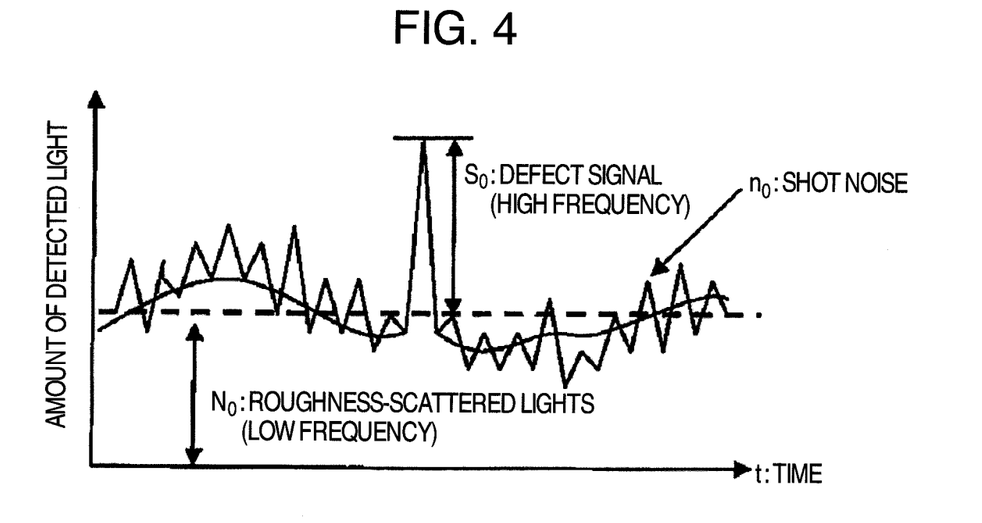
FIG. 4 graphically shows a signal detected in a pre-scan inspection.

FIG. 4 graphically shows a signal detected in a pre-scan inspection. Upon detecting the scattered lights emanating from the irradiated area, the sensors output such a signal as shown in FIG. 4. Roughness-scattered lights $N_o$ emanating from the rough surface of the wafer exist always during the irradiation with laser and are detected as a low frequency undulation (<several kH). When the roughness-scattered lights $N_o$ are received by the sensors and photo-electrically converted, shot noise $n_o$, i.e. random fluctuations, is generated and also detected simultaneously. On the other hand, since defect-scattered lights $S_o$ emanating from a defect are produced only during a short period of time while the irradiating spot having a diameter of about 20 micrometers passes over the position where the defect exists, the defect-scattered lights $S_o$ look like a higher frequency undulation (>several kH) as compared to the roughness-scattered lights $N_o$. In fact, when the detected signals shown in FIG. 4 are received by the analog circuit 150a, a defect signal can be extracted by causing them to pass through a high-pass filter (i.e. passband>several kH) while a roughness-scattered light intensity (hereafter referred to as Haze signal) can be extracted by causing them to pass through a low-pass filter (i.e. passband<several kH).

As described above, the electric signal resulting from the defect-scattered lights detected by the sensors is sent through the high-pass filter whereas the electric signal resulting form the roughness-scattered lights detected by the sensor is sent through the low-pass filter. Accordingly, it becomes possible to separately process the defect signal and the Haze signal. The filtered signal is then converted to a digital signal through a sampling process with a sampling frequency higher than several MHz by the A/D conversion section 151a. The resulting digital signal is fed to the defect determining section 152a and there subjected to the defect determination using threshold processing, the defect dimension calculation depending on defect signal intensity, the classification of defects depending on the comparison of the signal from the one detection system with the signal from the other detection system, and the Haze processing depending on level determination. And the inspection information obtained here, such as the coordinates and dimensions of the detected defects, is stored in the memory 153.

[Step 163]

Upon completion of pre-scan, the near-field head 10 is elevated relative to the wafer surface by a vertical distance of about 40 nm, and then near-field light is emitted from the fine aperture 15 cut in the front tip of the near-field head 10, to perform surface inspection.

Figure 5:
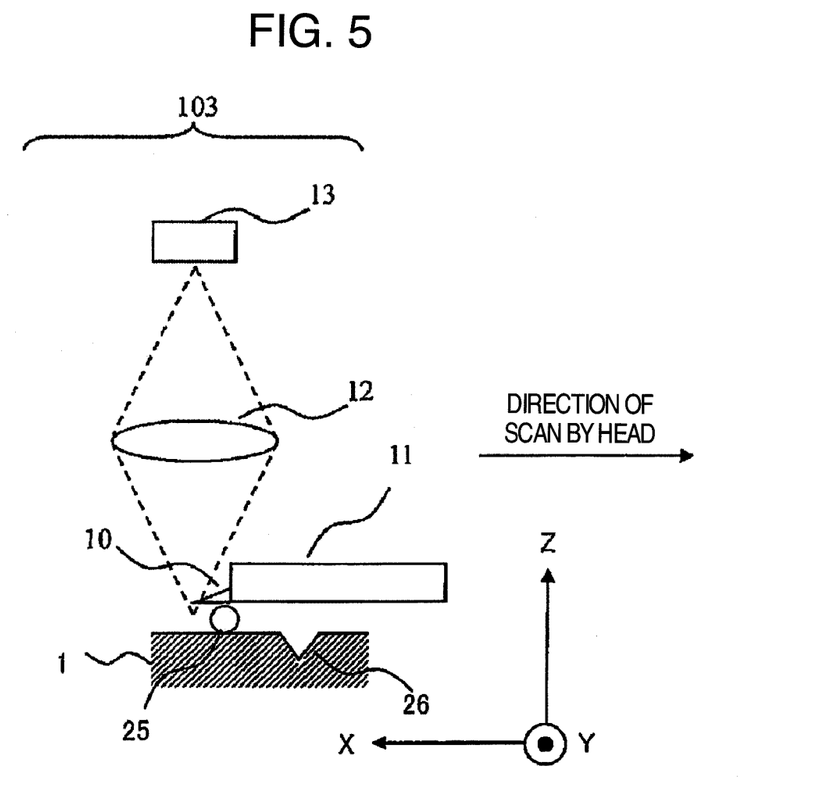
FIG. 5 schematically shows the structure of a head slider inspecting section.
Figure 14:
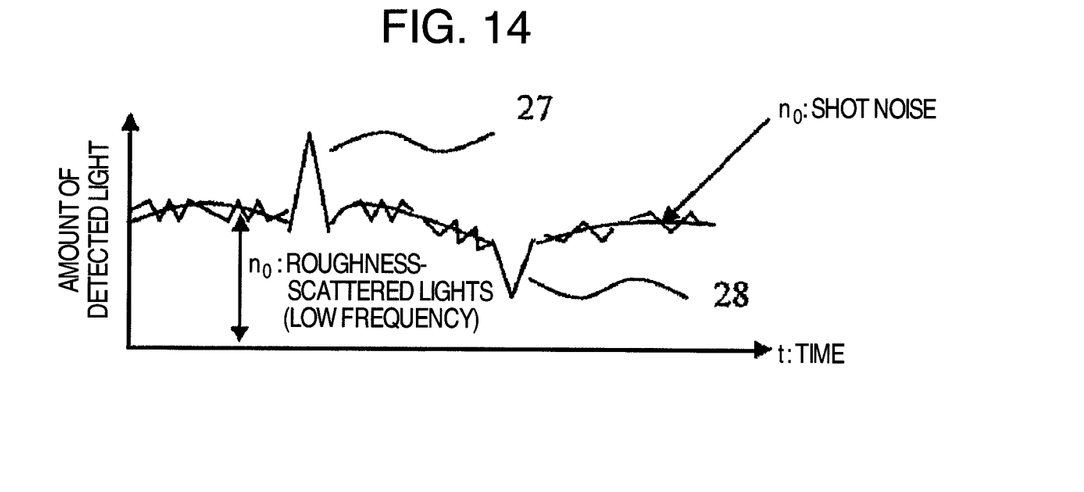
FIG. 14 graphically shows a signal detected in an inspection using a head slider.

FIG. 5 schematically shows the structure of a head slider inspecting section, illustrating how a raised defect 25 and a depressed defect 26 are scanned and how a signal reflecting those defects is detected. FIG. 14 graphically shows a signal detected in an inspection using a head slider.

As in the pre-scan, roughness-scattered lights $N_o$ (<several kH) emanate from the rough surface of the wafer. When the roughness-scattered lights NO are photo-electrically converted, shot noise $n_o$ is generated and simultaneously detected. In the area where there is the raised defect 25, the distance between the wafer surface and the fine aperture becomes small so that the interaction between the near-field light and the raised defect becomes intensified. As a result of this, scattered lights 27 (>several kH) having high intensities are instantaneously generated. On the other hand, in the area where there is the depressed defect 26, the distance between the wafer surface and the fine aperture becomes large so that the interaction between the near-field light and the depressed defect becomes weak. Hence, the detected signal exhibits a local depression 28, reflecting scattered lights (>several kH). Such a composite signal is fed to the analog circuit 150b, and there passes through a high-pass filter (passband>several kH). Consequently, a defect signal can be extracted.

The defect signal, after the above filtering process, is converted to a digital signal through a sampling process with a sampling frequency higher than several MHz by the A/D conversion section 151b. The resulted digital signal is fed to the defect determining section 152b and there subjected to the defect determination using threshold processing, the defect dimension calculation depending on defect signal intensity, and the defect classification depending on the dimensions of defects on a two-dimensional MAP and the fluctuation of the detected light amounts. At this time, a defect is determined to be a raised one if the detected light amounts increase, or to be a depressed one if the detected light amounts decrease.

[Steps 164, 165]

In step 162, since the coordinates of raised defects having dimensions greater than about 40 nm are stored in the memory 153, the vertical distance from the wafer surface of the near-field head 10 is adjusted according to the coordinates and the dimensions.

In the case where there is a raised defect having dimensions greater than about 40 nm in an area which will come under inspection by the near-field head 10 after several rotations of the wafer, the vertical distance controlling section 154 calculates the amount of current to be fed to the thermal actuator 17, in accordance with the dimensions of the raised defect, allowing the calculated current to be fed to the thermal actuator 17. Consequently, the thermal actuator 17 thermally expands to increase the vertical distance so that the collision of the near-field head with the raised defect can be avoided. When the near-field head has passed the area of the raised defect, the vertical distance controlling section 154 suppresses the current to be fed to the thermal actuator 17 so that the vertical distance is restored to about 40 nm to continue the inspection.

[Step 166]

Since defects having dimensions greater than about 40 nm are detected in step 162 and since defects having dimensions smaller than about 40 nm are detected in step 163, then these two results of detection are merged in the inspection result merging section 155.

[Step 167]

Figure 6:
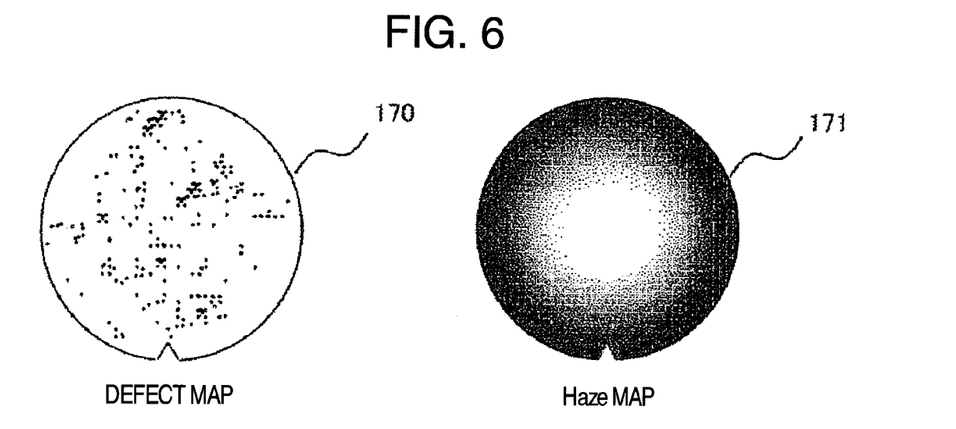
FIG. 6 illustrates a defect map and a haze map.

The merged result is supplied to the CPU 156 and the output of the CPU 156 is fed to the map outputting section 157 to display a defect map 170 and a Haze map 171 as shown in FIG. 6. The defect map 170 is generated on the basis of the types of defects, the dimensions of defects and the detected coordinates of defects, included in the inspection information obtained as a result of merging performed in the inspection result merging section 155. The Haze map 171 is generated on the basis of the level of the Haze signal and the detected coordinates of defects, included in the inspection information obtained as a result of merging performed in the inspection result merging section 155. The input section 158 includes a user interface by which a user performs recipe setting, etc.

FIG. 1 shows an embodiment of this invention wherein the pre-scan optical system has an irradiation optical system and an inspection optical system having different angles of elevation with respect to the wafer surface. This embodiment has two advantages as follows.

In an inspection wherein a raised defect to be detected is a foreign particle sticking onto the wafer surface, the scattering cross section of the particle appears to be greater for the laser irradiation slanting to the wafer surface than for the laser irradiation in the direction perpendicular to the wafer surface. With this arrangement, therefore, the amounts of scattered lights emanating from the raised defect are large so that even finer defects can be detected. Further, since the scattered lights from defects having dimensions of several tens of nm tend to intensely emanate at low elevation angles while those from defects having dimensions greater than several hundreds of nm tend to intensely emanate at high elevation angles, then fine defects can be detected by a low elevation angle inspection system while relatively large defects can be detected by a high elevation angle detection system, so that the range of sizes of detectable defects can be made larger.

On the other hand, in the case of depressed defects in the wafer surface, such as COP's or scratches, the scattering cross section of the depressed defect appears to be greater for the laser irradiation in the direction perpendicular to the wafer surface. Therefore, such a perpendicular irradiation allows the sensitivity of detection for depressed defects to be improved. Moreover, since the scattered lights from depressed defects tend to intensely emanate at high elevation angles, even higher sensitivity in detection can be achieved by using a high elevation angle detection system.

As described above, since the distribution and the characteristic depending on elevation angles, of the intensities of scattered lights emanating from defects change depending on the types (particle, COP or scratch) and dimensions of defects, precisions in the defect classification and the calculation of defect dimensions can be improved through comparisons using combinations of signals from different irradiating and detecting directions.

Figure 7:
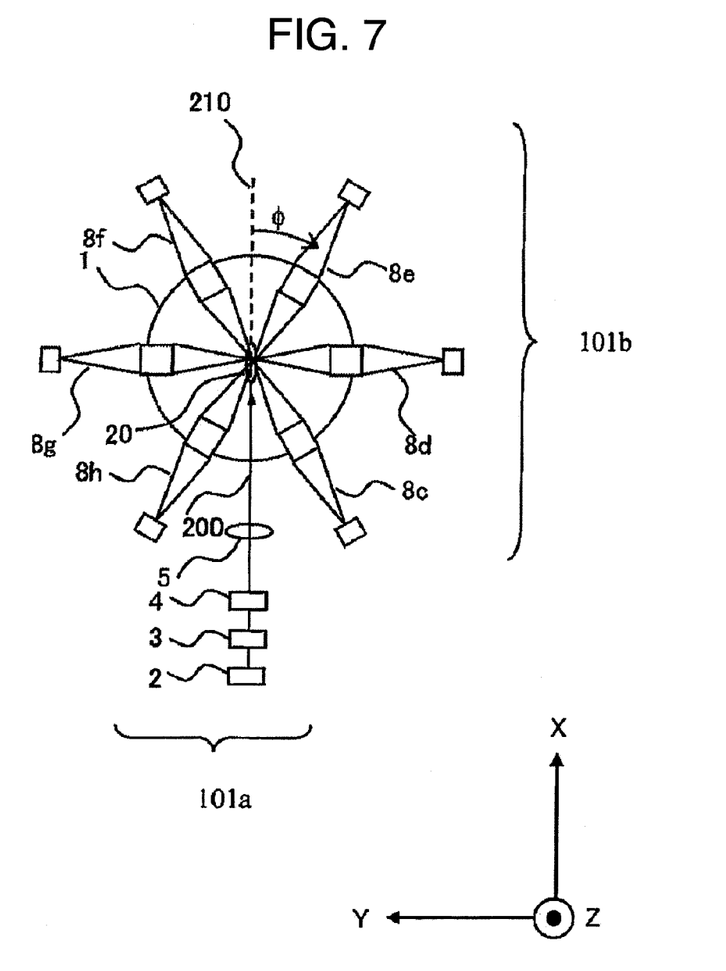
FIG. 7 schematically shows (in plan view) the structure of a pre-scan optical system in a result inspecting device according to this invention.

FIG. 7 schematically shows (in plan view) the structure of a pre-scan optical system in a result inspection device according to this invention. This pre-scan optical system is a variation of the pre-scan optical system 101 shown in FIG. 1. The pre-scan optical system comprises an irradiation optical system 101a and a detection optical system 101b, and the detection optical system 101b includes six detection optical systems 8c~8h. These detection optical systems 8c~8h are arranged at different azimuthal angles Φ's to detect scattered lights emanating from the irradiated area 20 on the wafer surface. The detection optical systems 8c~8h are separated from one another by an azimuthal angle Φ of 60°, located respectively at about 30, 90, 150, 210, 270 and 330 azimuthal degrees with respect to a certain reference azimuthal angle.

The advantage that detection takes place at a plurality of azimuthal angles is to be able to improve the sensitivity of detecting defects by selectively using desired detection optical systems or by weighting the signals detected by the detection optical systems. Roughness-scattered lights have an azimuthal angle dependency depending on the roughness of the wafer surface. For example, in the case of a Si wafer whose surface is very smooth, roughness-scattered lights tend to emanate intensely in the direction in which laser beam 200 impinges onto the wafer surface, i.e. at azimuthal angles at which the detection optical systems 8e and 8f are arranged. In the case of an aluminum-deposited film whose surface is very coarse, roughness-scattered lights tend to emanate intensely in the direction in which laser beam 200 travels, i.e. at azimuthal angles at which the detection optical systems 8c and 8h are arranged. Use is made of the signals detected only by the detection optical systems arranged at azimuthal angles at which roughness-scattered lights tend to emanate weakly. Or it becomes possible to improve the sensitivity of detecting defects by processing the detected signals such that they are multiplied by gains defined as weights proportional to the intensities of the roughness-scattered lights.

As shown in FIG. 7, laser irradiation is performed in a direction parallel to the longitudinal direction 210, but the direction for laser irradiation need not coincide with the longitudinal direction 210. Laser irradiation may be performed in an azimuthal direction different from the longitudinal direction 210. The advantage of the laser irradiation in an azimuthal direction different from the longitudinal direction 210 is that the performance in classifying such defects having a directional asymmetry with respect to their shapes as scratches can be improved. Defect-scattered lights emanating from such defects having an azimuthal symmetry as COP's do not have an azimuthal dependency but are diffused evenly in all the azimuthal directions. On the other hand, defect-scattered lights emanating from such defects having an azimuthal asymmetry as scratches are diffused in an azimuth-dependent manner. Moreover, since the azimuth-dependent characteristic of defect-scattered lights emanating from scratches depend also on the azimuthal angle of the optical axis of irradiation (i.e. laser beam), precisions in defect classification and calculation of dimensions can be improved by changing the direction of irradiation dynamically and comparing a signal from a detection system located at an azimuthal angle with another signal from another detection system located at another azimuthal angle.

In processing the signals detected by the detection systems arranged at a plurality of azimuthal angles and elevation angles, the process of addition or averaging is employed. The amount of detected lights increases as a result of addition, which results in an improvement in detection sensitivity. The averaging process increases the range of the sizes of detectable defects within the dynamic range of each sensor, and therefore leads to the increase in the resultant dynamic range of the sensors.

Figure 8:
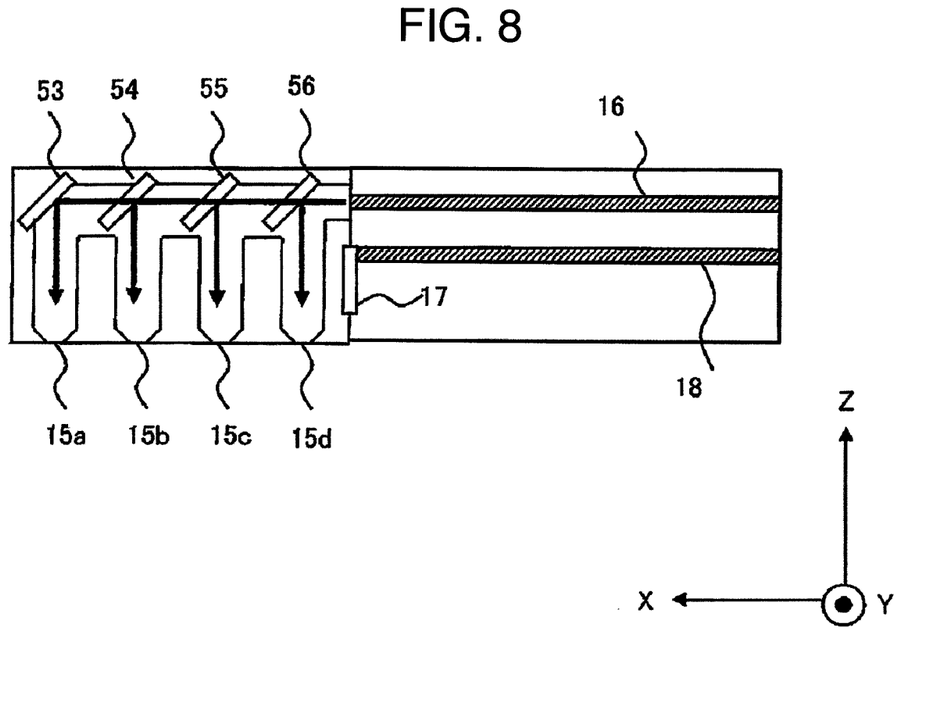
FIG. 8 schematically shows the structure of the near-field head of a defect inspecting device as a second embodiment of this invention.

In the embodiment shown in FIG. 2, the near-field head has a single fine aperture 15, but it may have a plurality of fine apertures as shown in FIG. 8. As shown in FIG. 8, laser beam traveling through a waveguide path 16 is split by means of a mirror 53 and half-transparent mirrors 54~56 into a plurality of beams, which reach fine apertures 15a~15d. Consequently, the respective fine apertures generate near-field, which can simultaneously irradiate a plurality of areas on the wafer surface. The fine apertures are separated from one another by a distance of about 300 nm. In this case, if the sensor 13 is provided with multiple pixels, the scattered lights generated due to the interaction between the near-field lights generated at the respective fine apertures and the wafer surface, can be detected separately on the pixels, respectively. This amounts to an increase in the effective inspection area per unit time. The sensor 13 may be implemented with a line sensor, a multi-anode PMT, a photodiode array, etc.

In the above description, the near-field head 10 is so constructed as to have a fine aperture at the tip of the head as shown in FIG. 2, but It may be constructed such that the fine aperture is replaced by a fiber probe as shown in FIG. 8.

Figure 9:
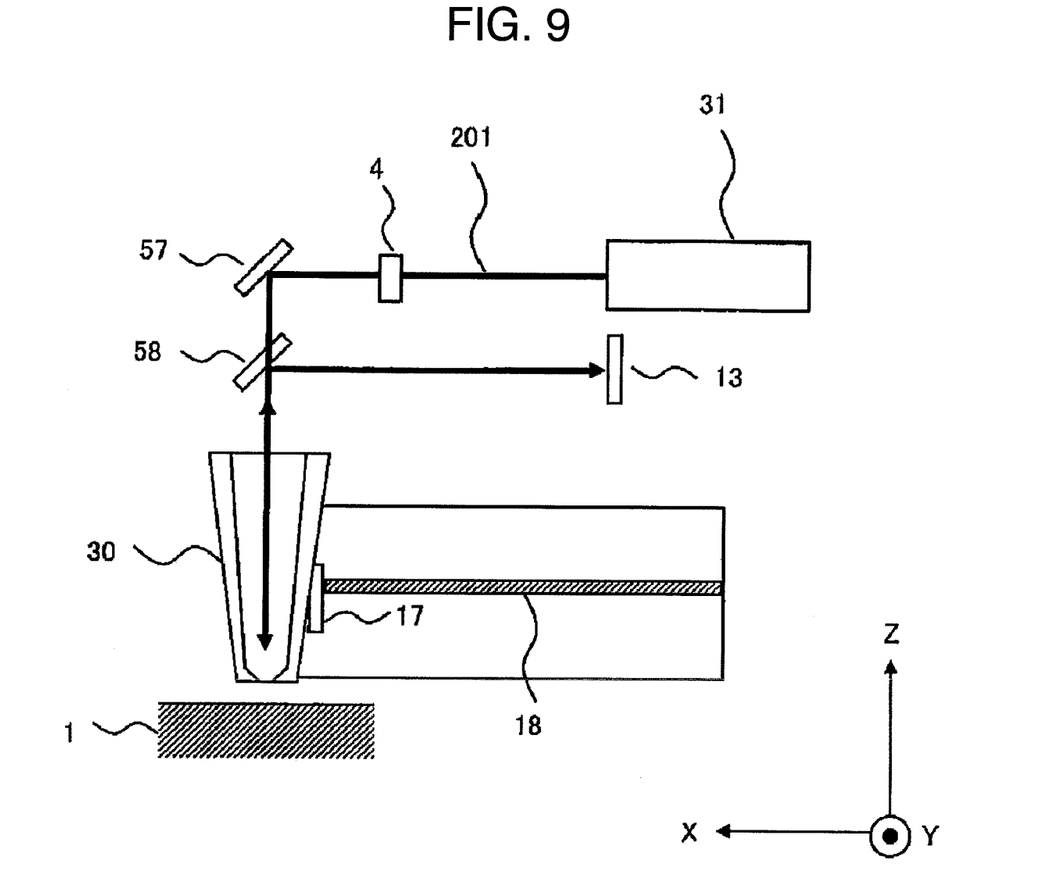
FIG. 9 schematically shows the structure of the near-field head using a fiber probe, of a defect inspecting device as a third embodiment of this invention.

FIG. 9 schematically shows the structure of a near-field head using a fiber probe, of a defect inspecting device as a third embodiment of this invention.

The tip of a fiber probe 30 is provided with a fine aperture having a diameter of several tens of nm. The fiber probe 30 is attached to the tip of the head, and the vertical distance thereof from the wafer surface is controlled by means of a thermal actuator 17. A laser beam 201 generated by a light source 31 is guided to the fiber probe 30 via a mirror 57, a half-transparent mirror 58 and a fiber coupler (not shown). The wavelength of the laser beam 201 emanating from the light source 31 is 532 nm. Accordingly, a near-field whose magnitude is about equal to the diameter of the fine aperture, is generated at the tip of the fiber probe 30. The near-field response resulted from the interaction between the near-field light and the wafer surface is detected by the fiber probe 30 itself. The detected light is guided through an optical fiber to a sensor 13.

Only a small fraction of the energy carried by the laser beam 201 will be consumed to excite the near-field. The rest of the energy is carried back as reflected lights traveling back through the probe. On the other hand, the near-field response detected by the fiber probe is very weak and therefore buried in the reflected lights. For this reason, such a very weak near-field response must be detected by a technique called "lock-in detection" using the vibration of the fiber probe. The fiber probe can be vibrated by, for example, a piezoelectric element (not shown) incorporated in the head.

In this way, the single fiber probe can perform both an irradiation and a detection functions, and this arrangement can dispense with an external detection system for the near-field response, leading to the simplification of the overall device.

Figure 10:
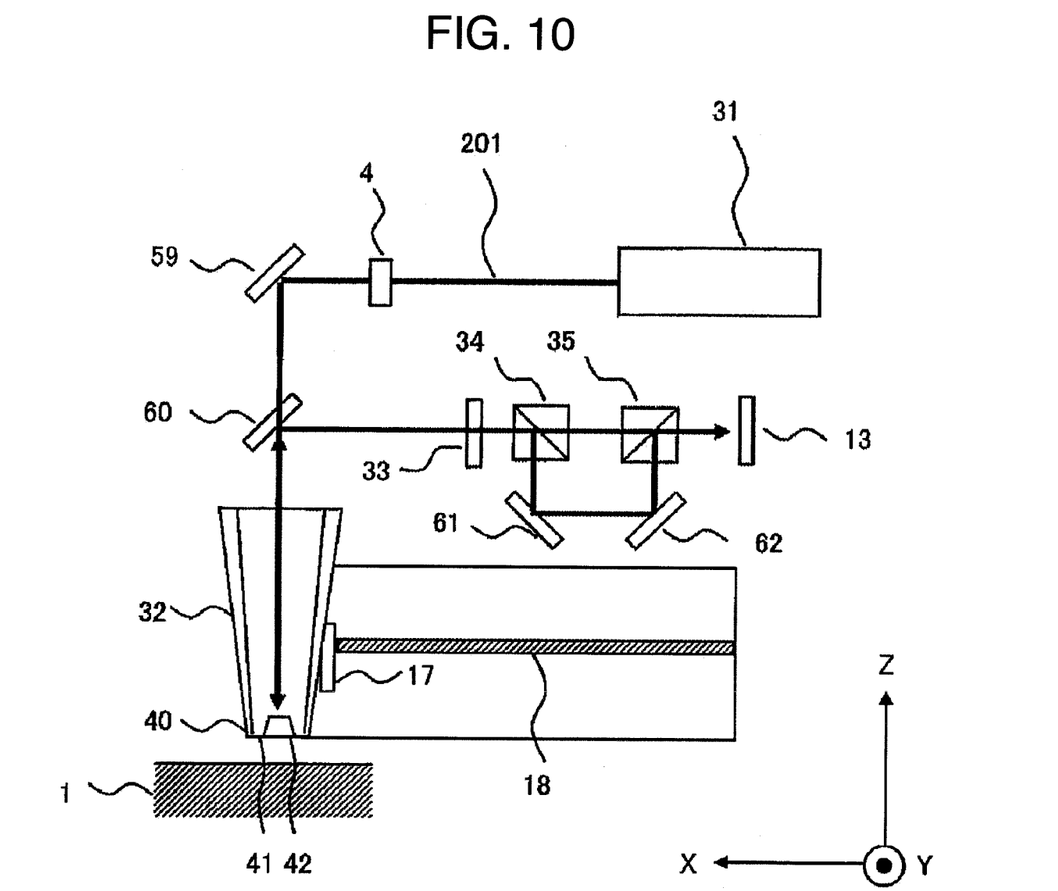
FIG. 10 schematically shows the structure of the near-field head using a fiber probe, of a defect inspecting device as a fourth embodiment of this invention.

FIG. 10 schematically shows the structure of a near-field head using a fiber probe, of a defect inspecting device as a fourth embodiment of this invention. A laser beam 201 emanating from alight source 31 is guided to a fiber probe 32 via a mirror 59, a half-transparent mirror 60 and a fiber coupler (not shown).

Figure 11:
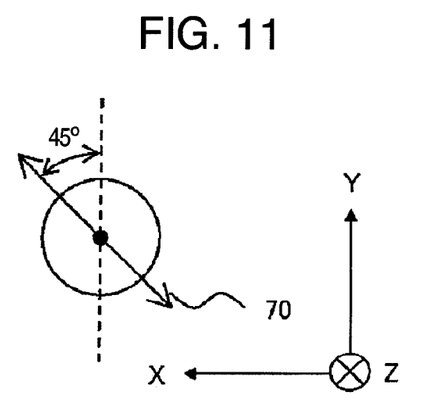
FIG. 11 illustrates the directions in which the electric field of the irradiating light oscillates.

FIG. 11 illustrates the directions in which the electric field of the irradiating light oscillates. This figure represents the oscillation of the electric field of the laser beam 201 as it enters the fiber probe 32. The directions 70 of oscillation of the electric field is perpendicular to the Z-axis and also subtends an angle of 45° with the X-axis.

There are rectangular openings 41 and 42 at the tip 40 of the fiber probe 32.

Figure 12:
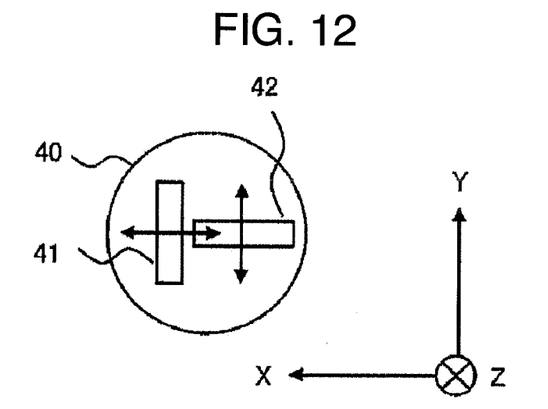
FIG. 12 shows in an enlarged view the tip of a fiber probe.
Figure 15:
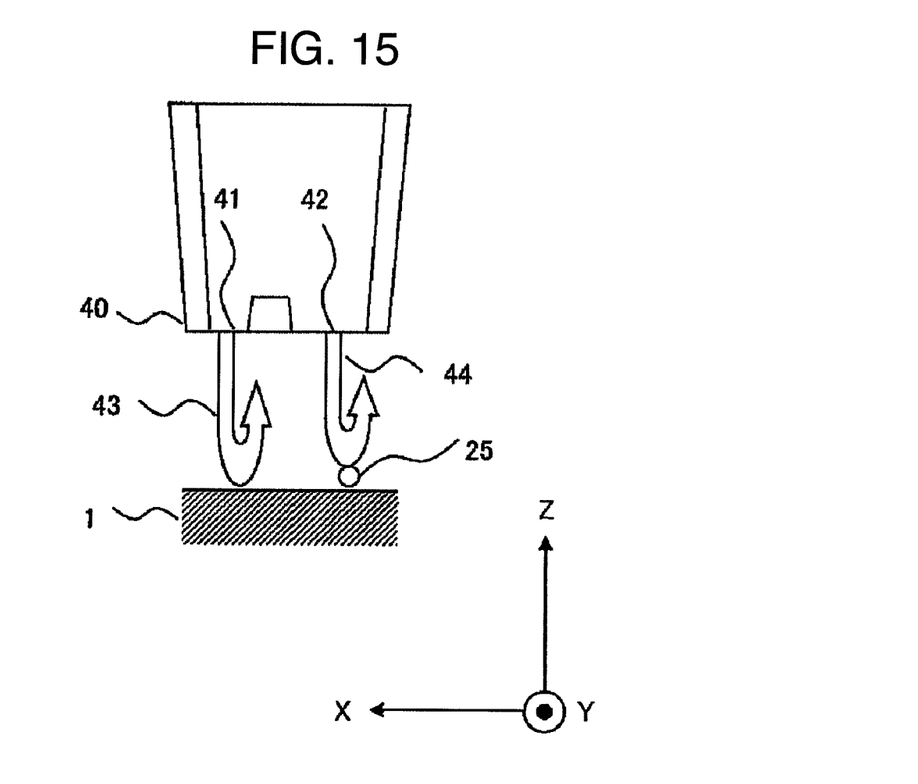
FIG. 15 shows in lateral and enlarged view the tip of a fiber probe.

FIGS. 12 and 15 show in an enlarged view and in a lateral and enlarged view, respectively, the tip of a fiber probe. Fine openings 41 and 42 are both rectangular, each having its lengthwise side of several tens of nm and widthwise side of about 20 nm (lengthwise dimension>widthwise dimension). It should be noted here that the dimensions of each fine opening are smaller than the wavelength of the laser beam. By forming the fine openings in the shape of a rectangle, only that electric filed of the laser beam which oscillates in parallel to the widthwise side of the fine opening can pass through the fine opening. In fact, by forming the fine openings 41 and 42 such that they are oriented perpendicularly with respect to each other, two kinds of polarized near-field lights having their polarization angles perpendicular to each other can come out from the fine openings 41 and 42. The lengthwise direction of the fine opening 41 is parallel to the Y-axis while the lengthwise direction of the fine opening 42 is parallel to the X-axis.

Figure 13:
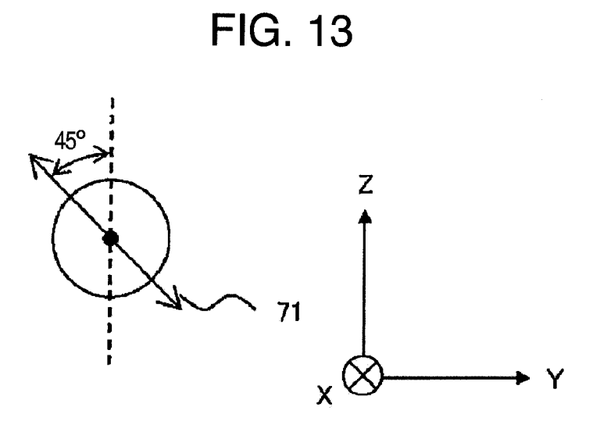
FIG. 13 illustrates the direction of the transmission axis for electric field in a polarizing element.

The inspections of the wafer surface are performed by using the near-field light 43 coming out of the fine opening 41 as reference light and the near-field light 44 coming out of the fine opening 42 as probing light. Further, the near-field responses are also detected by the fine openings 41 and 42. The detected two types of lights travel via a polarizing element 33, PBS's 34 and 35, and mirrors 61 and 62 and are detected by a sensor 13. FIG. 13 illustrates the direction of the transmission axis for electric field in the polarizing element 33. The axis for electric field transmission in the polarizing element 33 is perpendicular to the X-axis and subtends an angle of 45° with the Y-axis. PBS's 34 and 35 let the electric fields oscillating in the direction parallel to the Z-axis pass and let the electric fields oscillating in the direction parallel to the Y-axis be reflected. Accordingly, a light path difference occurs between the light traveling via the PBS's 34 and 35 and reaching the sensor 13, and the light traveling via the PBS's 34 and 35, and the mirrors 61 and 62 and reaching the sensor 13.

If there is a defect on the wafer surface, a phase difference occurs between the reference light and the probing light so that a change occurs in the signal detected by the sensor 13. The degree of the change depends on the distance between the defect 25 and the tip 40 of the probe. In fact, the defect can be detected as information indicating the associated distance.

The size of a defect can be calculated with higher precision by detecting the defect as information indicating the associated distance. Further, although it is difficult to detect a flat and thin defect such as a water mark by using scattered lights, it can be detected with high precision if an interference system is used where a defect is detected as information indicating the height of the defect.

In the flow chart shown in FIG. 3, the inspection by the head slider is performed after the entire wafer surface has been inspected in the pre-scan procedure. However, the inspection by the head slider may be started while the wafer surface is under inspection during the pre-scan procedure. Alternatively, the head slider inspection may be successively performed on those areas of the wafer surface which have got through the pre-scan inspection. The earlier the head slider inspection is started, the shorter is the time required for inspection.

The head slider inspection need not necessarily cover the entire surface of the wafer. The pre-scan inspection may cover only those areas on the wafer surface where it is difficult to discriminate defects from noise. By doing so, the time required for inspection can be shortened. In the above embodiment, in order to avoid the collision of a raised defect having a size larger than about 40 nm with the near-field head 10, the vertical distance of the head 10 is controlled depending on the results obtained in the pre-scan. However, it is not always necessary to inspect with the near-field head 10 those areas where there are raised defects larger than about 40 nm. Without performing inspections over such unwanted areas, the overall area to be inspected can be decreased and therefore the time required for inspection can be shortened.

As described above, the laser source 2 has a wavelength of 355 nm, but a laser source that emits visible, ultraviolet or vacuum-ultraviolet rays may be used instead.

As described above, the laser source 31 has a wavelength of 532 nm, but a laser source that emits visible, ultraviolet or vacuum-ultraviolet rays may be used instead.

As described above, the irradiated area 20 on the wafer surface has a rough elliptical shape with its major axis of about 100 µm and its minor axis of about 20 µm, but the shape of the irradiated area need not be an ellipse and the size thereof is not limited, either.

In FIG. 1, described is an embodiment wherein there are two inspection systems arranged at two different elevation angles $\theta_s$'s, but the number of such inspection systems is not limited to two.

In FIG. 7, described is an embodiment wherein there are six inspection systems arranged at six different azimuthal angles Φ's, but the number of such inspection systems is not limited to six. Further, there are no limitations to the numbers of the azimuthal angles Φ's, the elevation angles $\theta_s$'s, and the sizes of the fine apertures.

The sensors 9a and 9b are used to receive the scattered lights and to convert them to electric signals, and therefore they may be implemented with multi-anode photo-electron multipliers, TV cameras, CCD cameras, photodiodes, linear sensors or highly sensitive image sensors each being the combination of one of the preceding elements and an image intensifier. For example, if two-dimensional sensors are used, larger areas on the wafer surface can be inspected at a time.

There are no limitations to the size of the fine aperture 15, the number of fine apertures, the distance between separated fine apertures, and the sizes of fine openings at the tips of the fiber probes 30 and 32.

In the flow chart in FIG. 3, the pre-scan is performed to detect defects having a size larger than about 40 nm, but the size of defect is not limited to about 40 nm. Also, the vertical distance from the wafer surface of the near-field head 10 is not limited to about 40 nm.

As described hitherto, according to the embodiments of this invention, it becomes possible to detect defects having a size of 10~20 nm by scanning the wafer surface with the near-field head having a fine aperture of about several tens of nm and kept at a vertical distance of about several tens of nm from the wafer surface, and by detecting the near-field response resulting from the interaction between the near-field generated by the near-field head and the wafer surface.

Furthermore, according to this invention, a method and a device for inspecting defects which can avoid the collision of the near-field head with large defects by previously memorizing the coordinates of the large defects obtained through the pre-scan using the detection of the scattered lights before scanning with the near-field head, and by controlling the vertical distance from the wafer surface of the near-field head on the basis of the coordinates and the sizes of the large defects.

Reference Signs List 1 wafer; 2, 31 laser source; 3 beam expander; 4 polarizing element; 5 condensing lens; 6 rotating stage; 7 parallel-moving stage; 8a~8h detection systems; 9a, 9b, 13 sensors; 10 near-field head; 11 head supporting mechanism; 12 near-field response detection system; 15, 15a~15d fine apertures; 16 waveguide path; 17 thermal actuator; 18 conductor wire; 20 irradiated area; 25 raised defect; 26 depressed defect; 27, 28 defect signal; 30, 32 fiber probe; 33 polarizing element; 34, 35 PBS; 40 tip of fiber probe; 41, rectangular opening; 43 reference light; 44 probing light; 50~55, 57, 59, 61, 62 mirror; 54~56, 58, 60 half-transparent mirror; 70 direction of electric field oscillation; 71 transmission axis of polarizing element; 101 pre-scan optical system; 101a irradiation optical system; 101b detection optical system; 102 wafer stage; 103 head slider inspecting section; 104 signal processing section; 150a, 150b analog circuit; 151a, 151b A/D converting section; 152a, 152b defect determining section; 153 memory; 154 vertical distance controlling section; 155 inspection result merging section; 156 CPU; 157 map outputting section; 158 inputting section; 160~167 inspection flow chart; 170 defect map; 171 Haze map; 200, 201 laser beam; 210 lengthwise direction of irradiation

The invention claimed is:
1. A defect inspecting method comprising:
a pre-scan defect inspecting process including:
a pre-scan irradiating step for casting irradiation light onto the surface of a sample, a pre-scan detecting step for detecting the scattered lights emanating from the area of the sample surface irradiated in the pre-scan irradiating step, and a pre-scan defect information collecting step for obtaining information on preselected defects present on the sample surface on the basis of the scattered lights detected in the pre-scan detecting step;

a near-field defect inspecting process including:

a near-field irradiating step in which the distance between the sample surface and a near-field head is adjusted on the basis of the information on the preselected defects obtained in the pre-scan defect information collecting step so that the irradiation of the sample surface is started from the position where the near-field head has been adjusted, a near-field detecting step for detecting near-field light response generated from that area on the sample surface which is irradiated in the near-field irradiating step, and a near-field defect information collecting step for obtaining information on the preselected defects present on the sample surface on the basis of the near-field light response detected in the near-field detecting step; and a merging process for inspecting defects present on the sample surface on the basis of the result obtained by merging the information on the preselected defects on the sample surface obtained in the pre-scan defect information collecting step and the information on the preselected defects present on the sample surface obtained in the near-field defect information collecting step.

2. A defect inspecting method according to claim 1, wherein defects present on the sample surface and having sizes larger than a predetermined size are detected in the pre-scan defect information collecting step.

3. A defect inspecting method according to claim 1, wherein the information on the sizes and the positions of the preselected defects present on the sample surface is obtained in the pre-scan defect information collecting step.

4. A defect inspecting method according to claim 2, wherein defects present on the sample surface and having a diameter not less than 40 nm are detected in the pre-scan defect information collecting step.

5. A defect inspecting method according to claim 1, wherein in the near-field irradiating step, the distance between the near-field head and the sample surface is adjusted by controlling the amount of current conducted through an actuator that adjusts the position of the near-field head.

6. A defect inspecting method according to claim 5, wherein the amount of current is determined on the basis of the information on the preselected defects present on the sample surface, obtained in the pre-scan defect inspecting process.

7. A defect inspecting method according to claim 1, wherein raised defects present on the sample surface and having a diameter not larger than a predetermined value and depressed defects are detected in the near-field defect information collecting step.

8. A defect inspecting method according to claim 1, wherein raised defects present on the sample surface and having a diameter not larger than 40 nm and depressed defects are detected in the near-field defect information collecting step.

9. A defect inspecting device comprising:

a pre-scan defect inspecting section including:

a pre-scan irradiating system for casting irradiation light onto the surface of a sample, a pre-scan detecting system for detecting the scattered lights emanating from the area of the sample surface irradiated by the pre-scan irradiating system, and a pre-scan defect information collecting section for obtaining information on preselected defects present on the sample surface on the basis of the scattered lights detected by the pre-scan detecting system;

a near-field defect inspecting section including:

a near-field irradiating section in which the distance between the sample surface and a near-field head is adjusted on the basis of the information on the preselected defects obtained by the pre-scan defect information collecting section so that the irradiation of the sample surface is started from the position where the near-field head has been adjusted, a near-field detecting section for detecting near-field light response generated from that area on the sample surface which is irradiated by the near-field irradiating section, and a near-field defect information collecting section for obtaining information on the preselected defects present on the sample surface on the basis of the near-field light response detected by the near-field detecting section; and a merging section for inspecting defects present on the sample surface on the basis of the result obtained by merging the information on the preselected defects on the sample surface obtained by the pre-scan defect information collecting section and the information on the preselected defects on the sample surface obtained by the near-field defect information collecting section.

10. A defect inspecting device as claimed in claim 9, wherein defects present on the sample surface and having sizes larger than a predetermined size are detected by the pre-scan defect information collecting section.

11. A defect inspecting device according to claim 9, wherein the sizes and the positions of the preselected defects present on the sample surface are obtained by the pre-scan defect information collecting section.

12. A defect inspecting device according to claim 10, wherein defects present on the sample surface and having a diameter not less than 40 nm are detected by the pre-scan defect information collecting section.

13. A defect inspecting device according to claim 9, wherein the near-field irradiating section adjusts the distance between the near-field head and the sample surface by controlling the amount of current conducted through an actuator that adjusts the position of the near-field head.

14. A defect inspecting device according to claim 9, wherein the amount of current is determined on the basis of the information on the preselected defects present on the sample surface, obtained by the pre-scan defect inspecting section.

15. A defect inspecting device according to claim 9, wherein raised defects present on the sample surface and having a diameter not larger than a predetermined value and depressed defects are detected by the near-field defect information collecting section.

16. A defect inspecting device according to claim 9, wherein raised defects present on the sample surface and having a diameter not larger than 40 nm and depressed defects are detected in the near-field defect information collecting section.

* * * * *